(12) United States Patent
Santori et al.

(10) Patent No.: US 10,459,241 B2
(45) Date of Patent: Oct. 29, 2019

(54) IMAGING APPARATUS AND METHODS USING DIFFRACTION-BASED ILLUMINATION

(71) Applicant: Hewlett-Packard Development Company, L.P., Spring, TX (US)

(72) Inventors: Charles M Santori, Palo Alto, CA (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 291 days.

(21) Appl. No.: 15/307,759

(22) PCT Filed: Apr. 30, 2014

(86) PCT No.: PCT/US2014/036044
§ 371 (c)(1),
(2) Date: Oct. 28, 2016

(87) PCT Pub. No.: WO2015/167492
PCT Pub. Date: Nov. 5, 2015

(65) Prior Publication Data
US 2017/0052384 A1    Feb. 23, 2017

(51) Int. Cl.
*G02B 27/42* (2006.01)
*G02B 21/00* (2006.01)
(Continued)

(52) U.S. Cl.
CPC .......... *G02B 27/425* (2013.01); *G01N 21/05* (2013.01); *G02B 6/003* (2013.01); *G02B 6/0035* (2013.01);
(Continued)

(58) Field of Classification Search
CPC .... G02B 27/425; G02B 21/362; G02B 21/06; G02B 21/0004; G02B 21/00; G02B 6/003;
(Continued)

(56) References Cited

U.S. PATENT DOCUMENTS

| 6,535,638 B2 | 3/2003 | McGrew |
| 7,659,971 B2 | 2/2010 | Warden et al. |

(Continued)

FOREIGN PATENT DOCUMENTS

| CN | 101046624 | 10/2007 |
| CN | 103676130 | 3/2014 |
| WO | 2014053883 | 4/2014 |

OTHER PUBLICATIONS

Hahn et al., "Thin holographic camera with integrated reference distribution," Applied Optics, vol. 50, No. 24, pp. 4848-4854, Aug. 20, 2011 (7 pages).

(Continued)

*Primary Examiner* — Allen C Wong
(74) *Attorney, Agent, or Firm* — Hanley Flight & Zimmerman LLC (57) ABSTRACT

Imaging apparatus and methods using diffraction-based illumination are disclosed. An example apparatus includes a diffraction grating to redirect light from a light source toward a sample to thereby illuminate the sample. The example apparatus also includes an image sensor to detect a diffraction pattern created by the illuminated sample.

18 Claims, 10 Drawing Sheets

(51) Int. Cl.
| | | |
|---|---|---|
| *G02B 21/06* | (2006.01) | |
| *F21V 8/00* | (2006.01) | |
| *G03H 1/04* | (2006.01) | |
| *G01N 21/05* | (2006.01) | |
| *G02B 21/36* | (2006.01) | |
| *H04N 5/225* | (2006.01) | |
| *G03H 1/08* | (2006.01) | |
| *G03H 1/02* | (2006.01) | |
| *G03H 1/22* | (2006.01) | |
| *G03H 1/26* | (2006.01) | |
| *G03H 1/00* | (2006.01) | |

(52) U.S. Cl.
CPC ......... *G02B 21/00* (2013.01); *G02B 21/0004* (2013.01); *G02B 21/06* (2013.01); *G02B 21/362* (2013.01); *G03H 1/041* (2013.01); *G03H 1/0443* (2013.01); *G03H 1/0465* (2013.01); *H04N 5/2256* (2013.01); *G03H 1/0244* (2013.01); *G03H 1/0866* (2013.01); *G03H 1/265* (2013.01); *G03H 2001/0033* (2013.01); *G03H 2001/0447* (2013.01); *G03H 2001/0452* (2013.01); *G03H 2001/0469* (2013.01); *G03H 2001/0471* (2013.01); *G03H 2001/0473* (2013.01); *G03H 2001/2226* (2013.01); *G03H 2222/34* (2013.01); *G03H 2223/16* (2013.01); *G03H 2223/19* (2013.01); *G03H 2223/23* (2013.01); *G03H 2227/02* (2013.01); *G03H 2227/03* (2013.01); *G03H 2240/56* (2013.01)

(58) Field of Classification Search
CPC .... G02B 6/0035; G01N 21/05; H04N 5/2256; G03H 1/041; G03H 1/0443; G03H 1/0465; G03H 1/265; G03H 1/0244; G03H 1/0866; G03H 2001/0452; G03H 2001/0471; G03H 2001/0473; G03H 2001/0033; G03H 2001/0469; G03H 2001/2226; G03H 2001/0447; G03H 2223/23; G03H 2223/19; G03H 2223/16; G03H 2227/02; G03H 2227/03; G03H 2222/34; G03H 2240/56
USPC .......................................................... 348/79
See application file for complete search history.

(56) References Cited

U.S. PATENT DOCUMENTS

| | | | |
|---|---|---|---|
| 7,791,725 B2 | 9/2010 | Shishido et al. | |
| 8,530,811 B2 | 9/2013 | Molnar et al. | |
| 2004/0155309 A1* | 8/2004 | Sorin | G01N 21/253 257/433 |
| 2010/0177311 A1* | 7/2010 | Wada | G01N 15/0211 356/336 |
| 2011/0228263 A1 | 9/2011 | Chuang et al. | |
| 2012/0223217 A1 | 9/2012 | Zheng et al. | |
| 2012/0248292 A1 | 10/2012 | Ozcan et al. | |
| 2012/0320185 A1 | 12/2012 | Gohara et al. | |
| 2013/0003073 A1 | 1/2013 | Yu et al. | |
| 2013/0273524 A1 | 10/2013 | Ehrenkranz | |
| 2013/0293697 A1 | 11/2013 | Sun et al. | |
| 2013/0294724 A1* | 11/2013 | Li | G02B 6/12011 385/24 |
| 2014/0370581 A1* | 12/2014 | Saltsman | B01F 5/0473 435/287.2 |
| 2015/0204729 A1* | 7/2015 | Kusunose | G01B 9/02098 356/521 |
| 2015/0268421 A1* | 9/2015 | Higuchi | G02B 6/356 385/17 |

OTHER PUBLICATIONS

Isikman et al., "Lensfree On-Chip Microscopy and Tomography for Biomedical Applications," IEEE Journal of Selected TOICS in Quantum Electronics, vol. 18, No. 1, pp. 1059-1072, May/Jun. 2012 (14 pages).

Gurkan, U.A. et al., Miniaturized Lensless Imaging Systems for Cell and Microorganism Visualization in Point-of-care Testing, (Research Paper), Jan. 5, 2011.

* cited by examiner

IMAGING APPARATUS AND METHODS USING DIFFRACTION-BASED ILLUMINATION

BACKGROUND

Microscopic imaging is a useful tool with many applications. While image sensors (e.g., charge-coupled devices (CCD) or complementary metal-oxide-semiconductor (CMOS)) have seen a rapid drop in price used in many types of imaging systems, microscopes are still expensive due to the cost of the microscope objective (e.g., one or more optical lenses). Recently, lens-free imaging approaches have been developed that provide high resolution images that can cover substantial areas (e.g., exceeding what is possible with a conventional microscope objective at a relatively high magnification).

BRIEF DESCRIPTION OF THE DRAWINGS

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts.

DETAILED DESCRIPTION

Microscopic imaging systems can be used in a variety of applications such as in the medical industry. For example, with the large computational power now available in low-cost laptop computers and smartphones, much effort is being made to develop low-cost and portable medical diagnostic devices that can be powered by USB or similar interfaces to allow routine tests to be performed outside of a hospital. In this manner, the cost of such tests and the burden on patients is reduced.

Some medical diagnostic tests are accomplished through the use of an imaging system. Imaging systems can be beneficial in many applications such as counting cells for blood analysis, in counting bacteria, and/or in flow cytometry because the imaging systems allow reliable classification by size, color, shape, etc. In addition to medical applications, microscopic imaging systems are useful in non-biological settings such as water quality testing (e.g., counting and/or characterizing impurities and/or particulates in water). Another useful application for microscopic imaging systems is analyzing the surface of print media (e.g., paper) and/or the print quality (e.g., print dot size, shape, and/or placement) on such print media.

A limitation on the production of microscopic imaging systems is the cost of the optical element or microscope objective. To overcome this obstacle, recent efforts have been made to develop lens-free imaging systems. Some such lensless imaging techniques employ directional light to illuminate a mostly transparent sample placed in front of an image sensor (e.g., a CMOS sensor array) at close proximity (e.g., within several millimeters of the image sensor). As the directional light passes through the sample, some of the light will be scattered by the sample. The scattered light will interfere with light that continues to pass straight through the sample, thereby creating a diffraction pattern that can be picked up by the image sensor. To a human, the diffraction pattern may appear as blurry spots similar to what would result from an image captured by a camera with a dirty lens. Software algorithms are used to convert, deconvolve, and/or otherwise reconstruct the diffraction pattern into a useful (e.g., high resolution) image of the sample that is recognizable to a human eye. The reason for using directional light is that the entire sample is illuminated with light coming at the same angle to provide symmetry in the diffraction pattern across the sample area (e.g., corresponding to the area of the image sensor). That is, if light was incident upon the sample at different angles in different parts of the sample, the resulting diffraction pattern would be inconsistent across the captured image making it much more difficult to reconstruct an image of the sample.

Current lens-free approaches that employ this technique can develop relatively high-resolution images of relatively large sample areas that exceed what is possible through traditional microscopy at high levels of magnification. However, a disadvantage of such approaches is that, to achieve consistent directional illumination of the sample, the light source must be positioned relatively far away from the sample. Moreover, as the sample area increases there is typically a proportionate increase in the distance of the light source to maintain substantially directional light over the increasingly expansive area. Thus, known techniques involve light sources at appreciable distances (e.g., upwards of several centimeters) with some variation depending upon the size of the sample area being imaged. While the distance between the light source and the sample may be small enough to produce a portable imaging system, such systems are still bulky and, therefore, awkward to implement.

Examples disclosed herein use diffraction grating-based illumination to enable similar imaging performance but with a much smaller form factor than known techniques. In particular, low-cost, ultra-compact, and large-area lens-free imaging systems are disclosed that use diffraction gratings to achieve substantially flatter form factors than other known methods. In some examples, the vertical distance between a light source and a light sensor may be less than a few millimeters thick (e.g., approximately 1.5 mm to 5 mm). Such thin form factors may make integration with smartphones and/or other portable devices much more practical than currently known methods. Examples disclosed herein may be contained within a housing having a total height of less than one centimeter. Furthermore, unlike known approaches, the thickness of disclosed examples does not increase with an increasing sample area. The diffraction gratings in the disclosed examples may be employed to provide directional and uniform illumination of a sample. As used herein, "directional light" or "directional illumination" refers to light composed of light rays that are substantially parallel with each other (e.g., the angular uncertainty is relatively small or negligible). As used herein, "uniform illumination" of a sample refers to light that has substantially consistent intensity on any portion of the sample being illuminated relative to any other portion of the sample. Thus, directional and uniform illumination of a sample indicates that the sample may be illuminated substantially consistently throughout the entire imaging portion of the sample (e.g., the area of the sample being imaged) both in terms of the angle of incidence of the light and the intensity of the light.

In some disclosed examples, the diffraction grating may be combined with a slab waveguide where collimated light is introduced at one end. As the light travels along the waveguide and then comes in contact with the diffraction grating, the diffraction grating redirects the light to provide the directional light that is to illuminate a sample. Some disclosed examples implement the diffraction grating in a transmission mode where the directional light passes through the sample to an image sensor. Some disclosed examples may implement the diffraction grating in a reflection mode where the directional light passes through the sample and then is reflected back through the waveguide and the diffraction grating to an image sensor on the opposite side.

In some disclosed examples, the diffraction grating may be combined with an external point source of light (e.g., an un-collimated laser). In some such examples, the diffraction grating may be structured with circularly arced grooves or ridges centering around the point light source. In this manner, as light emanates from the point source in all directions, the light will contact the entire length of each groove uniformly to enable controlled redirection of the un-collimated (non-directional) light into directional light that can appropriately illuminate a sample of interest. More particularly, in such examples, the diffraction grating may be structured such that the light contacting each part of any particular groove has the same phase. Further, in such examples, the spacing of adjacent grooves are set to experience differences in phase of the incident light such that the light scattered in the desired direction (e.g., towards the sample) adds constructively for all the grooves to form the directional light.

Figure 1:
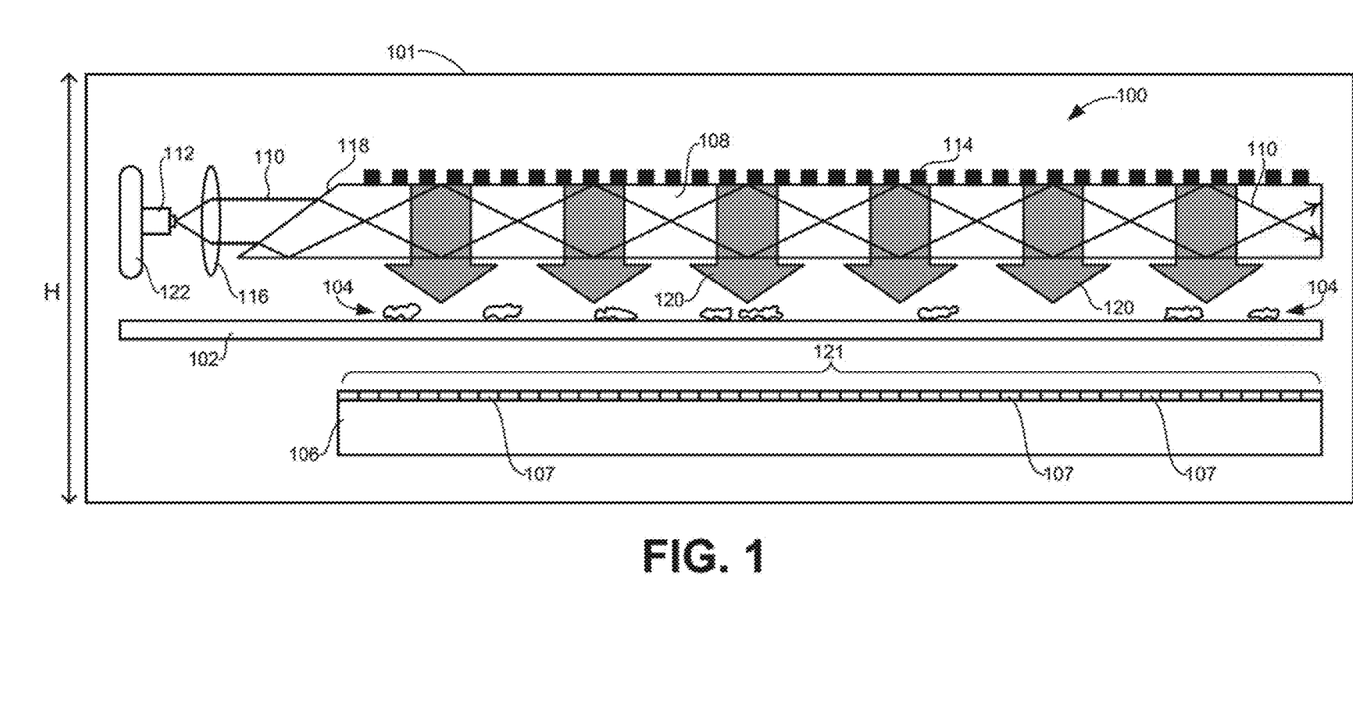
FIG. 1 is a cross-sectional schematic illustration of an example microscopic imaging system constructed in accordance with the teachings disclosed herein.

FIG. 1 is a cross-sectional schematic illustration of an example microscopic imaging system 100 constructed in accordance with the teachings disclosed herein. The example imaging system 100 includes a window 102 to hold a sample 104 adjacent an image sensor 106. The sample 104 may be any material(s) to be microscopically imaged in accordance with the teachings disclosed herein. In some examples, the sample 104 may be substantially transparent. In some examples, the sample 104 may be formed of non-transparent objects, particles, or particulates that can scatter light. In some examples, the sample 104 may be a substantially transparent fluid (e.g., liquid or gas) that contains substantially transparent and/or non-transparent objects, particles, or particulates. In some specific examples, the sample 104 may be biological in nature (e.g., a blood sample containing blood cells, pollen grains, bacteria, etc.) or non-biological (e.g., dust, powder, and/or other inorganic particulates. Further, in some examples, the sample corresponds to a printed image or a surface of a print medium for printing an image.

In some examples, the image sensor 106 may be implemented by a complementary metal-oxide-semiconductor (CMOS) sensor array. In other examples, the image sensor 106 may be implemented by a charge-coupled device (CCD) sensor array. Although the illustrated example shows a space or gap between the window 102 and the image sensor 106, in some examples the window 102 and the image sensor 106 are directly abutting or in contact with each other. In some such examples, the distance between the sample 104 and the image sensor 106 approximately corresponds to the thickness of the window 102. Further, in some examples, a slab waveguide 108 may be positioned close to the sample with little or no gap beyond the thickness of the sample itself. Thus, in some examples, the total thickness of the imaging system 100 approximately corresponds to the combined thickness of the image sensor 106 (e.g., approximately 1 mm thick), the window 102 (e.g., approximately 0.5 mm to 1 mm thick, including any sensor-window gap), the sample 104 (e.g., approximately 0.1 mm to 1 mm thick), and the waveguide 108 (e.g., approximately 1 mm to 2 mm thick). Thus, in some examples, this total thickness may be less than about five millimeters and can be less than about 2.5 millimeters. In some examples, the imaging system 100 may be contained within a housing 101 that has a total height H of one centimeter or less.

The example imaging system 100 of FIG. 1 includes the slab waveguide 108 positioned adjacent the sample 104 to transmit a beam of collimated or substantially collimated light 110 from a light emitter 112 from an end of the slab waveguide 108 along its length. As used herein, "substantially collimated light" refers to light that is collimated to a degree possible in view of physical realities such as manufacturing tolerances (e.g., of the collimating lens 116) and the area of the light emitter 112. In the illustrated example, a diffraction grating 114 is located adjacent a surface of the waveguide 108. In the illustrated example, as the beam of collimated light 110 travels along the waveguide 108, the light interacts with the diffraction grating 114. As the beam of collimated light 110 comes into contact with the diffraction grating 114, the light may be redirected toward the sample 104 as described more fully below.

In some examples, the waveguide 108 may be made of a dielectric material such as glass or plastic. In the illustrated example, the light from the light emitter 112 may be collimated into the beam of light 110 via a collimating lens 116. That is, the rays of light emitted from the light emitter 112 are made parallel (or substantially parallel as permitted by the physical realities (e.g., manufacturing tolerance) of the selected collimating lens) before entering the waveguide. In some examples, the light emitter 112 may be implemented by a laser diode. In some examples, the light emitter 112 may be implemented by a light-emitting diode (LED).

In some examples, the angle of incidence of the beam of collimated light 110 inside the waveguide 108 is controlled to be larger than the critical angle (e.g., approximately 42 degrees for a glass-air interface) such that the beam of collimated light 110 is confined within opposing surfaces of the slab waveguide 108 due to total internal reflection. In this manner, light is not lost (or only negligibly lost) as it travels along the waveguide 108. Additionally, in some examples, the angle of incidence of the beam of collimated light 110 may be controlled more precisely at an angle larger than the critical angle based on a desired efficiency of the diffraction grating 114 (e.g., how much light the diffraction grating redirects when it is contacted by the beam of collimated light 110). For examples, light travelling along the waveguide 108 at an angle of incidence that is too large (e.g., approaching parallel with the surfaces of the waveguide 108) will not bounce back and forth along the waveguide 108 very many times reducing the amount of interaction with the diffraction grating 114. Thus, relatively little light will be redirected by the diffraction grating 114. On the other hand, light travelling along the waveguide 108 at an angle of incidence that is too small (even if still above the critical angle) may bounce so many times that the diffraction grating 114 will redirect too much of the light before it has traveled the entire length of the waveguide 108. In this situation (e.g., too much light redirection), there may be insufficient light to adequately illuminate the sample 104 below the far end of the waveguide 108 resulting in non-uniform illumination of the sample 104. More particularly, in some examples, the angle or range of angles of incidence suitable for the beam of collimated light 110 inside the waveguide 108 depends upon the structure (e.g., period and height of grooves or ridges) of the diffraction grating 114, the structure (e.g., thickness) of the waveguide 108, the diameter of the beam of collimated light 110, and the size of the sample region requiring illumination (which affects the length of the waveguide). In some examples, a suitable range for the angle of incidence of the beam of collimated light 110 inside the waveguide 108 may be between about (e.g., +/−1 degree) 55 degrees and about (e.g., +/−1 degree) 75 degrees.

In some examples, as shown in FIG. 1, the desired angle of incidence may be achieved via an angled leading facet 118 of the slab waveguide 108. In some examples, the light emitter 112 and the collimating lens 116 are placed out of parallel alignment with the slab waveguide 108 and/or at a specific angle relative to the angle of the leading facet 118 to achieve the desired angle of incidence of light within the waveguide.

As mentioned above, in the illustrated example, the waveguide 108 is associated with the diffraction grating 114 that is structured to redirect light from the beam of collimated light 110 travelling along the waveguide 108 toward the sample 104 and image sensor 106. As shown in the illustrated example of FIGS. 1 and 2, the diffraction grating 114 includes a series of parallel linear structures extending across a surface of the waveguide 108 substantially perpendicular (e.g., within +/−1 degree) to the direction of travel of the beam of collimated light 110. In some examples, the linear structures of the diffraction grating 114 are formed from slits, grooves, or channels etched within the surface of the waveguide 108. That is, in some examples, the structure of the diffraction grating 114 may be integrally formed from the material of the slab waveguide 108. In some examples, the structure of the diffraction grating 114 corresponds to strips, ridges, or ribs added onto the surface of the slab waveguide 108. In some examples, such ridges are formed by depositing metal or other material (e.g., a dielectric) onto the surface of the waveguide and then etching away portions of the deposit.

Although the cross-section of the ridges and/or grooves of the diffraction grating 114 of the illustrated example are square in shape, the cross-sectional shape and/or the depth and/or width of the grooves (or corresponding ridges) can be altered in keeping with the teachings disclosed herein. Further, the spacing or period between adjacent ones of the grooves or ridges can be appropriately adjusted without departing from the teachings disclosed herein. In particular, while the beam of collimated light 110 will remain inside the slab waveguide 108 because of total internal reflection, when the beam of collimated light 110 comes in contact with the diffraction grating 114, the light will be scattered or redirected in a different direction to escape the waveguide 108. The particular angle(s) at which light is diffracted and the amount of light that is diffracted is determined by the structure of the diffraction grating 114 and the angle of incidence of the beam of collimated light 110 inside the slab waveguide 108. In some examples, the diffraction grating 114 may be constructed to redirect light from the beam of collimated light 110 toward the sample 104 at an angle substantially perpendicular or normal to (e.g., within +/−1 degree of perpendicular) the waveguide 108 to illuminate the sample 104 at an angle substantially perpendicular or normal to (e.g., within +/−1 degree of perpendicular) the window 102 and/or the image sensor 106. In other examples, the diffraction grating 114 may be structured to redirect light toward the sample 104 at an angle other than perpendicular to the waveguide 108, the window 102, and/or the image sensor 106.

For purposes of explanation, the portion of the beam of collimated light 110 redirected toward the sample 104 is referred to herein as sample light 120 and is represented in the illustrated example with the shaded arrows. Because the beam of light 110 is collimated (e.g., formed of parallel or substantially parallel rays of light) and it enters and propagates through the slab waveguide 108 at a controlled angle, the resulting rays of the sample light 120 generated by the diffraction grating 114 are also parallel or substantially parallel with each other. That is, the sample light 120 is directional. However, unlike the collimated light 110 that is focused in a narrow beam of light within the waveguide 108, the sample light 120 may be dispersed over the entire area of the sample 104 associated with a sensor region 121 of the image sensor 106. As a result, the entire sample 104 may be illuminated by directional light such that any particular region of the sample is illuminated by light at the same or substantially the same angle of incidence. In this manner, the resulting light patterns detected by the image sensor 106 will be substantially consistent at each location within the sensing region 121. That is, in such examples, there will be greater symmetry between light (and the corresponding resulting diffraction pattern) in different areas within the sample image that can facilitate or improve post processing. In some examples, where precise directional illumination is less of a concern, the diffraction grating 114 may be replaced with a light scattering surface (e.g., a roughened surface) to scatter light toward the sample 104 to illuminate the sample 104 with light of less directional consistency.

In operation, the imaging system 100, of the illustrated example of FIG. 1, captures microscopic images of the sample 104 by providing light from a light emitter 112 that is collimated via the collimating lens 116 and introduced into the waveguide 108 at a controlled angle where it remains confined by total internal reflection between opposing surfaces. In some examples, as the beam of collimated light 110 propagates along the slab waveguide 108, the beam interacts with the diffraction grating 114 to generate the sample light 120. In particular, the diffraction grating 114 redirects a portion of the beam of light 110 (e.g., the sample light 120) toward the sample 104. In some examples, the diffraction grating 114 may be structured to control the angle at which the sample light 120 is diffracted and directed towards the sample 104. In the illustrated example, the sample light 120 may be directional light with an angle of incidence on the sample 104 substantially normal (e.g., within +/−1 degree of perpendicular) to the image sensor 106. In some examples, as the sample light 120 reaches the sample 104 it illuminates the sample 104. In particular, while some of the sample light 120 passes straight through the sample 104 toward the image sensor 106, some of the sample light 120 will scatter off of the objects, particles, or particulates in the sample. In some examples, interference between these two signals (e.g., the light passing through the sample 104 and the light bouncing off of the sample 104) on the image sensor 106 produce diffraction or interference patterns (e.g., blurry dark rings) in the captured image data. In some examples, the diffraction patterns of the captured image data are processed (e.g. by deconvolution) to reconstruct an image of the sample 104.

In some examples, the microscopic image produced using the example imaging system 100 described above has a resolution corresponding to the pixel spacing of the image sensor 106. For example, individual photo-detectors 107 of current CCD and/or CMOS sensor arrays have a size and spacing of a few micrometers. The smaller the spacing of the photo-detectors 107 of the image sensor 106 are, the higher the resolution (greater detail) of the resulting image. Traditional microscopes achieve greater detail by increasing the magnification of the microscope. However, such magnification typically comes at the cost of decreasing the field of view of the microscope. In contrast, increasing the detail in the example imaging system 100 may be accomplished by decreasing the pixel spacing (based on smaller individual photo-detectors 107) but the field of view remains constant corresponding to the entire sensing region 121 of the image sensor 106. Further, the size of an image sensor 106 (e.g., the area of its sensing region 121) can be any suitable size based on the number of individual photo-detectors 107 placed in the sensor array. Typically, the primary limiting factor in sensor array size is the cost to manufacture such an array. Thus, while a traditional microscope may have a field of view limited to a few millimeters wide at a certain magnification, in some examples, comparable microscopic images could be captured with a field of view (e.g., sample area) spanning across several centimeters or more. As such, examples disclosed herein can provide a much more expansive field of view than the field of view possible with a traditional microscope at a high level of magnification.

While the resolution of captured images corresponds to the pixel spacing of the image sensor 106, in some examples, sub-pixel resolution (e.g., resolution corresponding to less than the pixel spacing) may be possible if the captured image data includes multiple exposures of the sample 106 illuminated by directional light at different angles of incidence. In some examples, different angles of the directional sample light 120 are achieved by altering the angle of incidence of the collimated beam of light 110 inside the slab waveguide 108. By changing the angle of the collimated beam of light 110 inside the waveguide 108, the angle at which the light interacts with the diffraction grating 114 changes, thereby changing the resulting angle at which the sample light 120 is redirected toward the sample 104. In some examples, the angle of the collimated beam of light 110 may be altered by changing the position of the light emitter 112 with respect to the collimating lens 116. For instance, as shown in the illustrated example of FIG. 1, the imaging system 100 includes a mechanical actuator 122 coupled to the light emitter 112 to move the light emitter 112 relative to the rest of the imaging system 100. In some examples, the collimating lens 118 and/or the waveguide 108 are moveable relative to the rest of the imaging system by a similar mechanical actuator.

Figure 2:
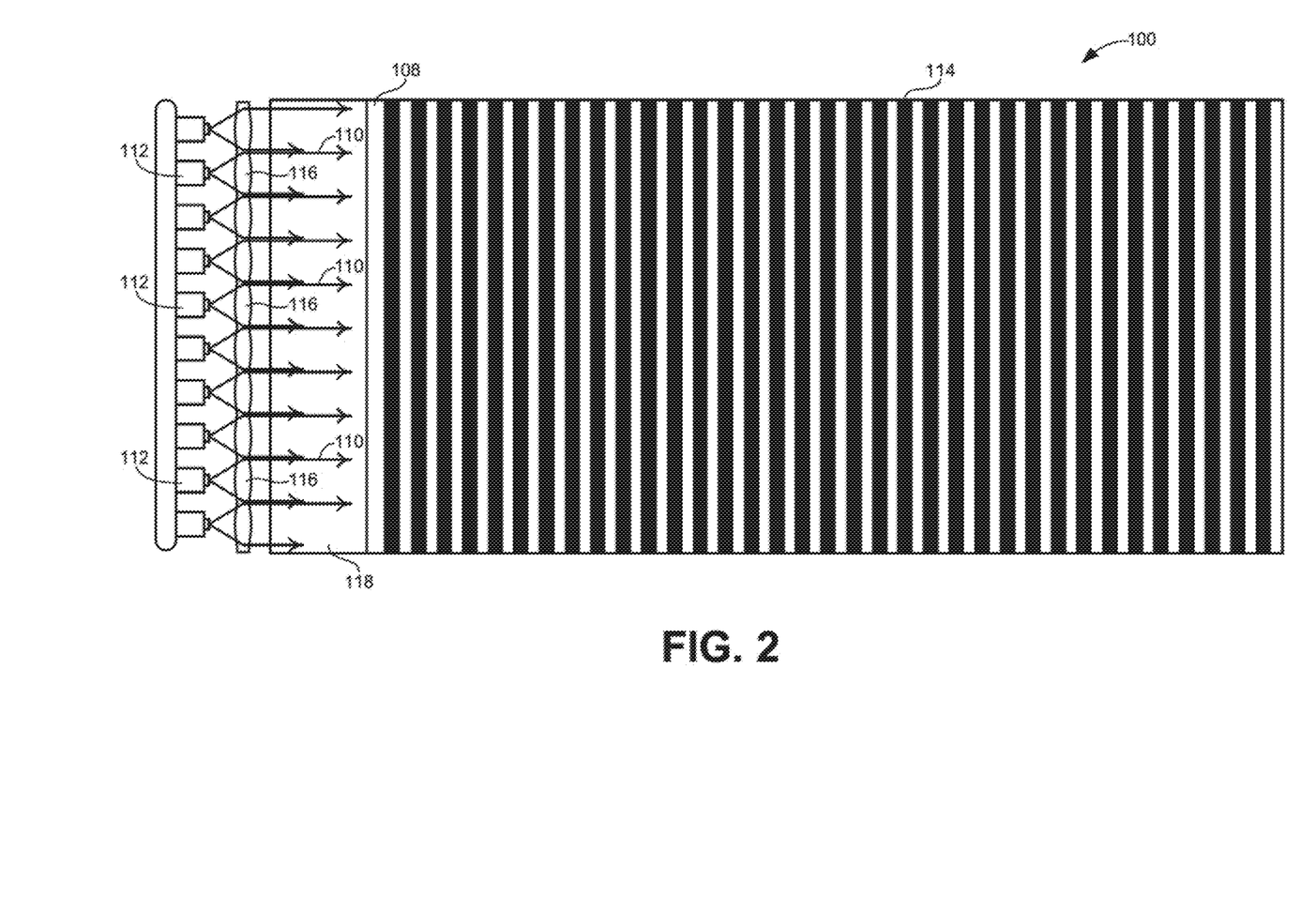
FIG. 2 is a top-view of the example microscopic imaging system of FIG. 1.

FIG. 2 is a top-view of the example microscopic imaging system of FIG. 1. As described above, the image sensor 106 can be any suitable size based on the number and arrangement of individual photo-detectors 107 in the sensor array. In some examples, the size of the image sensor 106 defines the size of the sample area, which in turn, defines an appropriate length and width (e.g., area) of the waveguide 108. Because the image sensor 106 can be of any suitable size, in some examples, the width of the image sensor 106 (and corresponding sample 104 and waveguide 108) is larger than the width of a single collimating beam of light 110. Accordingly, in some examples, the light source to illuminate the sample 104 may be provided from a plurality of light emitters 112. In some examples, the light from each of the plurality of light emitters 112 may be collimated via a respective one of a plurality of collimating lenses 116 to produce corresponding beams of collimated light 110 that together form a collimated light blanket to be transmitted along the waveguide 108. In some examples, the combined width of the collimated beams of light 110 corresponds to the width of the sensor region of the image sensor 106. In this manner, as the light blanket propagates along the slab waveguide 108 and is redirected by the diffraction grating 114, the entire sample is illuminated with directional light. In some examples, the collimating lenses 116 are made from a single unitary piece of material, as shown in the illustrated example, because of the proximity of the light emitters 112.

Figure 3:
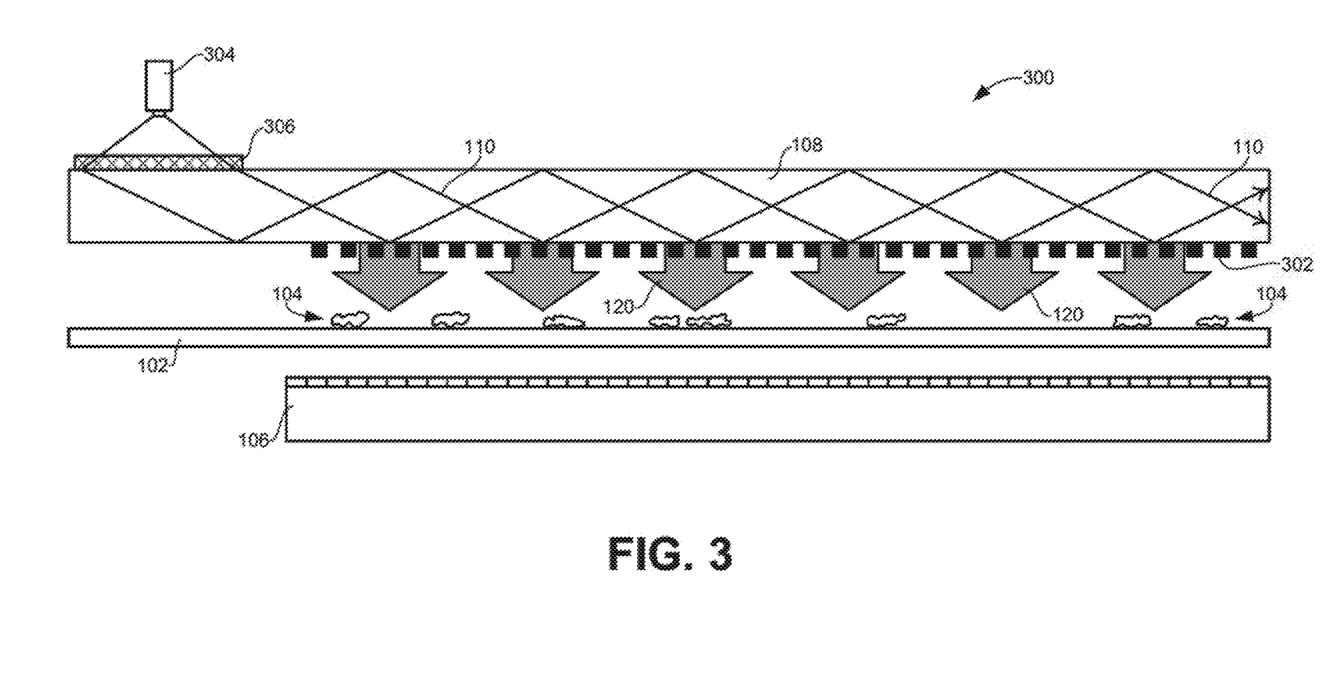
FIG. 3 is a cross-sectional schematic illustration of another example microscopic imaging system constructed in accordance with the teachings disclosed herein.

FIG. 3 is a cross-sectional schematic illustration of another example microscopic imaging system 300 constructed in accordance with the teachings disclosed herein. The example imaging system 300 of FIG. 3 is similar to the example imaging system 100 of FIG. 1 except that the imaging system 300 of FIG. 3 includes a diffraction grating 302 on the surface of the waveguide 108 facing toward the sample 104 rather than the surface facing away from the sample 104 as in FIG. 1. The example imaging system 300 of FIG. 3 operates in substantially the same manner as the imaging system of FIG. 1. However, the specific structure of the diffraction grating 302 and/or the angle of incidence of the collimating beam of light 110 inside the waveguide 108 may differ from the example in FIG. 1 to generate the sample light 120 that is diffracted away from the waveguide 108 (instead of across the waveguide 108 as in FIG. 1) and toward the sample 104 at the desired angle.

Additionally, in the illustrated example of FIG. 3, the imaging system 300 does not include the light emitter 112 and the collimating lens 116 at the end of the waveguide 108 as shown in FIG. 1. Rather, in the illustrated example of FIG. 3, the imaging system 300 includes a light emitter 304 that shines uncollimated light toward a grating coupler 306 to couple the light to the slab waveguide 108. In some examples, the grating coupler 306 includes one or more diffraction grating structures to interact with the light to make it collimated (or substantially collimated) and control the angle of incidence within the waveguide 108, thereby creating the collimated beam of light 110 that travels along the waveguide 108. Although the grating coupler 306 of the illustrated example is shown on the top surface of the waveguide 108 adjacent the light emitter 304, in some examples, the grating coupler 306 may be placed on the opposite surface of the waveguide 108 (e.g., where the diffraction grating 302 is located) such that the light from the light emitter 304 first passes through the waveguide 108 until it reaches the opposite side where the grating coupler 306 is located. In some such examples, as the light interacts with the grating coupler 306, the grating coupler 306 collimates the light into the beam of light 110 that is reflected back along the waveguide 108 at the desired angle of incidence to then be redirected by the diffraction grating 302 as the directional sample light 120 to illuminate the sample 104.

Figure 4:
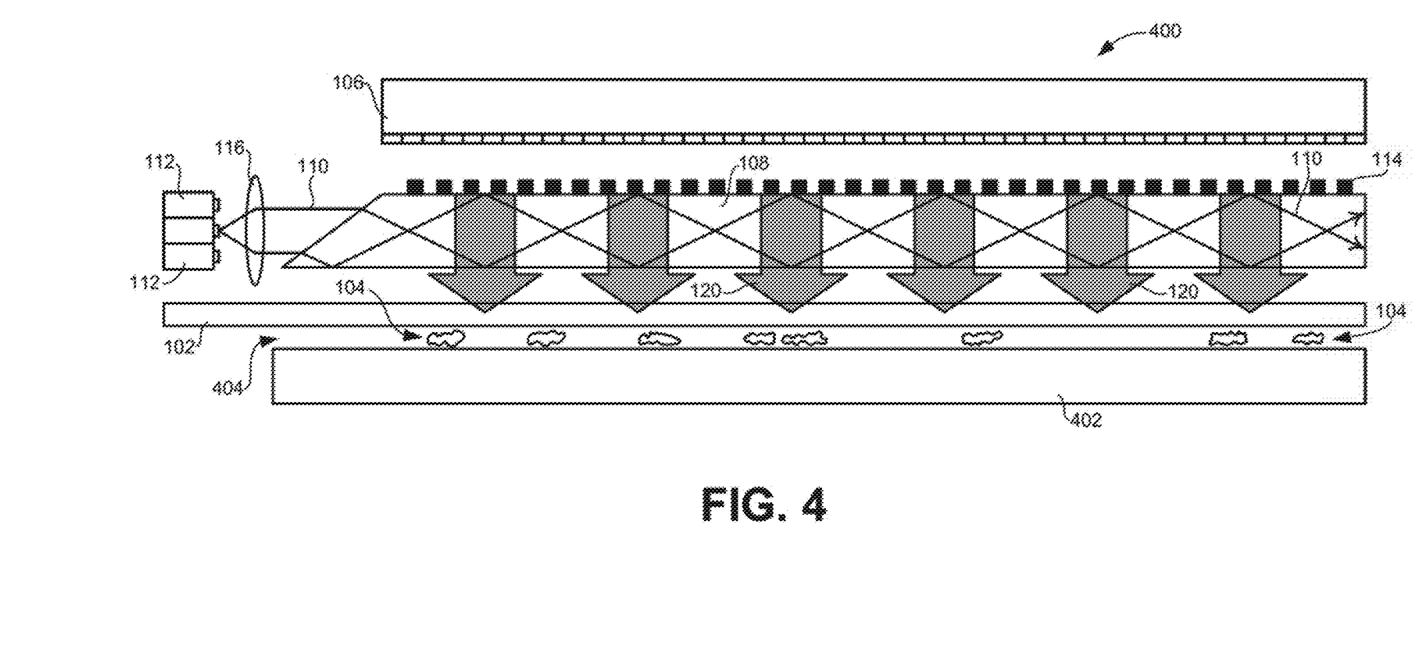
FIG. 4 is a cross-sectional schematic illustration of another example microscopic imaging system constructed in accordance with the teachings disclosed herein.

FIG. 4 is a cross-sectional schematic illustration of another example microscopic imaging system 400 constructed in accordance with the teachings disclosed herein. The example imaging system 400 of FIG. 4 is similar to the example imaging system 100 of FIG. 1 except that the slab waveguide 108 of the imaging system 400 of FIG. 4 is disposed between the sample 104 and the image sensor 106. In contrast, in the example imaging system 100 of FIG. 1, the sample 104 is disposed between the slab waveguide 108 and the image sensor 106. Although the illustrated example of FIG. 4 shows a space or gap between the waveguide 108 (and associated diffraction grating 114) and the image sensor 106, in some examples the waveguide 108 and the image sensor 106 are directly abutting or in contact with each other. Further, although the illustrated example of FIG. 4 shows a space or gap between the waveguide 108 and the window 102, in some examples the waveguide 108 and the window 102 are directly abutting or in contact with each other. In this manner, the distance between the sample 104 and the image sensor 106 approximately corresponds to the combined thickness of the window 102 and the waveguide 108 (e.g., as thin as approximately 1 mm to 1.5 mm).

In some examples, the window 102 and the waveguide 108 are close together because the sample 104 is not resting on the window 102 (as is the case in FIG. 1). Rather, the sample 104 may be below the window 102 and resting on a device layer 402 associated with the imaging system 400. In some examples, the window 102 may be omitted and the waveguide 108 may be against or approximately against the sample 104. In some examples, the device layer 402 may be a silicon substrate. In the illustrated example of FIG. 4, as the sample light 120 is directed toward the sample 104, some of the light will pass through the sample and be reflected back off of the device layer 402 while some of the light will be scattered by and/or reflected back off of the objects, particles, and/or particulates in the sample 104. In some examples, the reflected light travels back through the window 102 and the waveguide 108 before being captured by the image sensor 106 for post processing. Thus, the teachings disclosed herein are useful in a transmission mode (where light is transmitted through the sample 104 to be detected by the image sensor 106 as in FIGS. 1-3) or in a reflection mode (where light is reflected off of the sample 104 and then detected by the image sensor 106 as in FIG. 4).

While the extra pass through the waveguide 108 and diffraction grating 114, in such an example, may cause some additional interference relative to examples that do not exhibit the extra pass, this approach is a solution to circumstances where the device layer 402 is non-transparent. In some examples, the device layer 402 may be non-transparent because it is part of a microfluidic system. In some such examples, the gap or space between the window 102 and the device layer 402 may be a microfluidic channel 404. In some examples, the microfluidic channel 404 may be coupled to a pump to cause the sample 104 to flow through the microfluidic channel. In this manner, counting and/or distinguishing cells and/or particles as part of flow cytometry can be performed. Further, while traditional flow cytometry distinguishes cells based on principles of reflection and scattering of light, because examples disclosed herein generate images of the sample, the cells can also be distinguished based on other characteristics such as, for example, color, shape, size, etc.

The reflection mode described in FIG. 4 is also beneficial in imaging non-transparent samples. For instance, in some examples, the sample 104 may be a printed image (e.g., text, picture, etc.) on a print medium (e.g., paper). In some examples, using the teachings disclosed herein, the print quality (e.g., dot size, dot shape, dot spacing, etc.) can be microscopically imaged and analyzed. In some examples, the sample may be a type of print media (e.g., high gloss paper, cardstock, etc.) without any printed image to be microscopically imaged to analyze the surface quality of the print media.

Additionally, in the illustrated example of FIG. 4, the imaging system 400 does not include a mechanical actuator 122 to move the light emitter 112 as shown in the example imaging system 100 of FIG. 1. Rather, as shown in the illustrated example of FIG. 4, the imaging system 400 includes a plurality of light emitters 112 positioned differently relative to the collimating lens 116. By selectively activating one or more of the different light emitters 112, the angle of incidence of the resulting collimated beam of light 110 inside the waveguide 108 will result in different angles of the directional sample light 120 on the sample 104. In this manner, images of the sample 104 can be generated with resolutions finer than the pixel spacing of the image sensor 106 (e.g., sub-pixel resolution) as described above.

Figure 5:
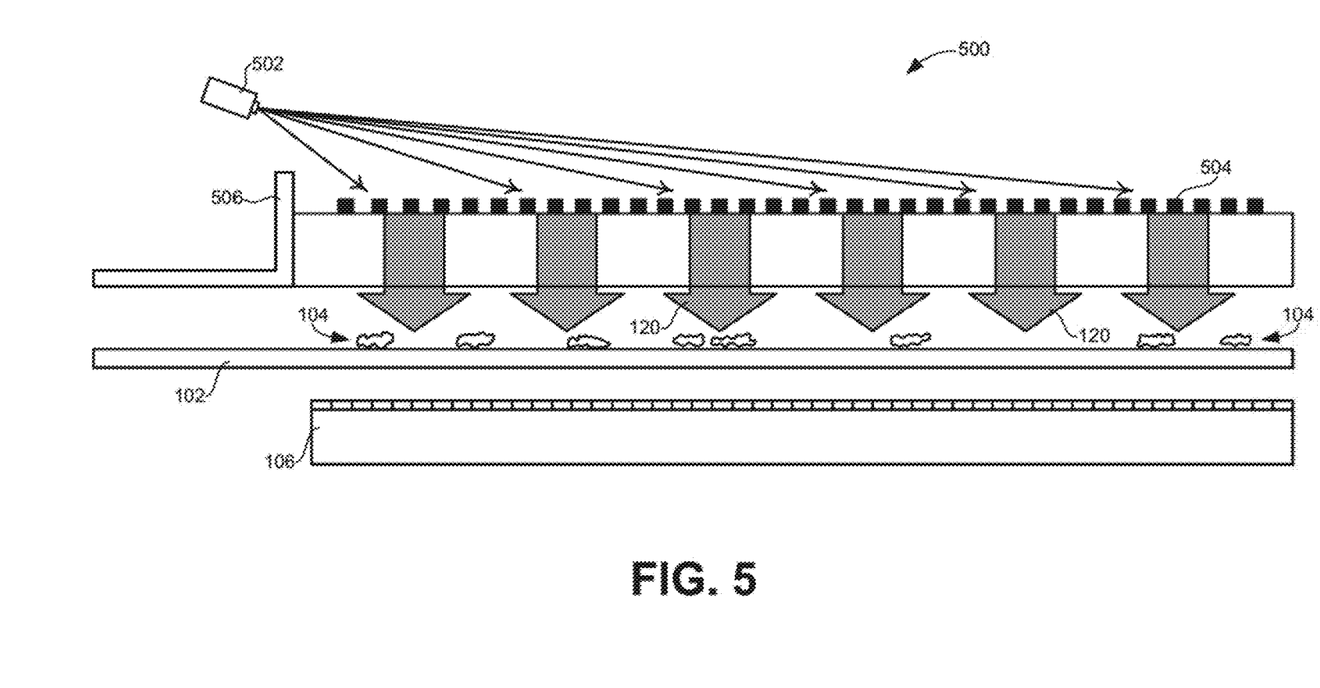
FIG. 5 is a cross-sectional schematic illustration of another example microscopic imaging system constructed in accordance with the teachings disclosed herein.

FIG. 5 is a schematic illustration of another example microscopic imaging system 500 constructed in accordance with the teachings disclosed herein. Unlike the example imaging systems 100, 300, 400 of FIGS. 1-4, the example imaging system 500 of FIG. 5 does not rely on collimated light coupled to a waveguide. Rather, as shown in the illustrated example of FIG. 5, the imaging system 500 includes a light emitter 502 that may be an un-collimated point source (e.g., shining light outward from a point in all directions). In the illustrated example, the light emitter 502 may be positioned off to the side of the sample 104 and the image sensor 106 at a slight elevation such that the light shines on a diffraction grating 504 at a relatively shallow angle relative to the plane of the diffraction grating 504. In some examples, the elevation of the light emitter 502 above the diffraction grating 504 (e.g., in a direction normal to a plane defined by the diffraction grating) may be approximately two to five millimeters such that the total thickness (e.g., approximately 4 mm to 10 mm) of the example imaging system 500 may be substantially less than other known lens-free imaging systems where the light source is placed at an appreciable distance from the sample because the light is directly above the sample. Using a shallow angle of light in this manner enables the light emitter 502 to be positioned much closer to the rest of the imaging system 500 than examples using a less shallow angle (e.g., directly above the sample), thereby substantially reducing the overall form factor (e.g., thickness or height) of the system when compared to other lens free microscopic imaging systems known in the art. In some examples, the imaging system 500 includes a light shield 506 to block light from the light emitter 502 from directly shining on the sample 104. In some examples, a lens (e.g., a cylindrical lens) may be disposed in front of the light emitter 502 to shape the angular distribution of the light such that a larger portion of the light will be incident on the diffraction grating 504.

In the illustrated example, as the uncollimated light meets the diffraction grating 504, the diffraction grating redirects the light to be directional and angled toward the sample 104 at a desired angle to illuminate the sample 104. Because the light originally emanates from a small, point-like source (e.g., the light emitter 502), the angle of the light incident on the diffraction grating 504 will be different at every location on the diffraction grating. For example, the angle of the light is shallower at portions of the diffraction grating 504 farther away from the light emitter 502 as is demonstrated in FIG. 5. Further, the direction of the light does not travel parallel in the plane of the diffraction grating 504 but diverges from a central axis aligned with the location of the light emitted as illustrated in a top view of the example imaging system 500 shown in FIG. 6.

Figure 6:
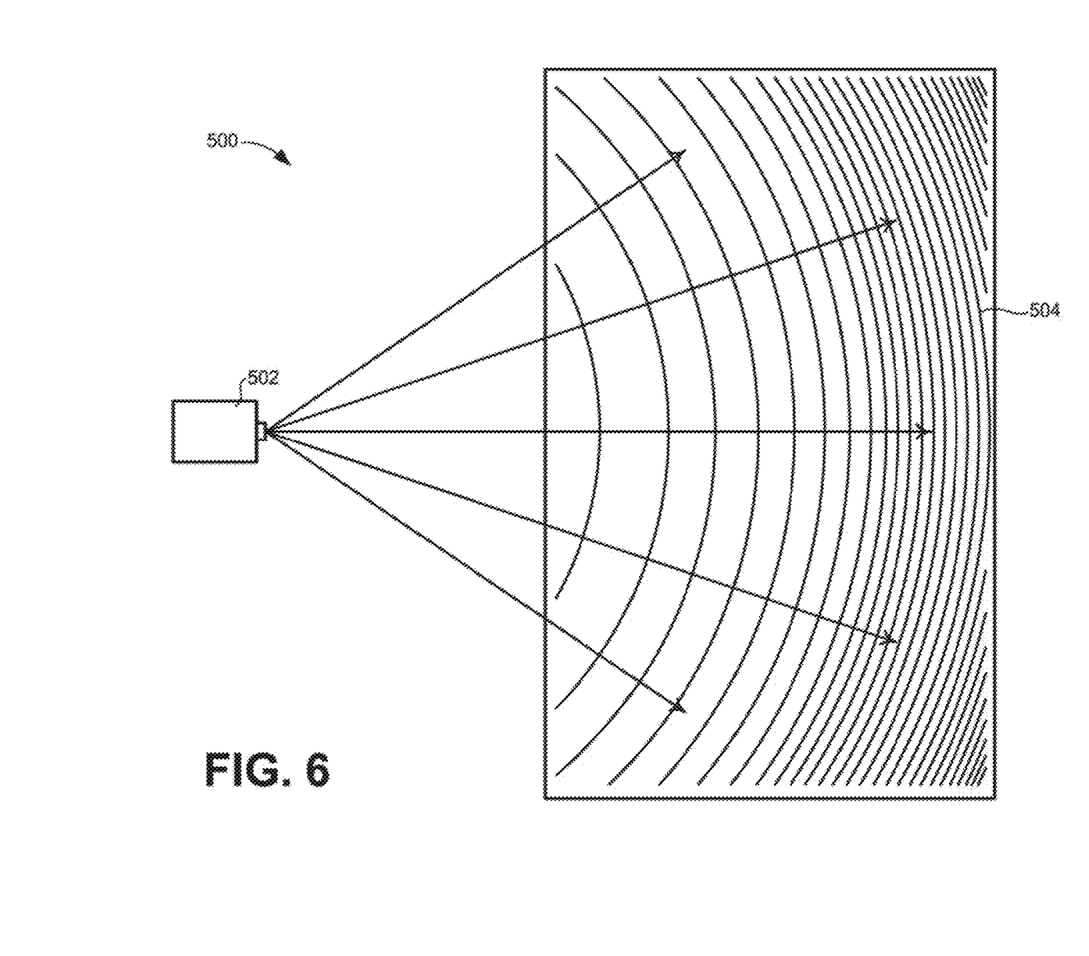
FIG. 6 is a top-view of the example microscopic imaging system of FIG. 5.

Accordingly, in some examples as shown in FIG. 6, the individual ridges or grooves of the diffraction grating 504 are structured as concentrically circular arcs with the point source of the light emitter 502 as the center point. In this manner, the light meets each ridge or groove at an angle substantially perpendicular to the tangent of any of ridges or grooves at any point on the diffraction grating 504. That is, the light interacts with the ridges or grooves in the same manner (e.g., same relative direction) regardless of the angle of the light in the plane of the diffraction grating 504.

Further, as shown in the illustrated examples, the period or spacing between adjacent ones of the ridges or grooves of the diffraction grating 504 changes depending on the distance away from the central axis of the grooves or ridges defined by the light emitter 502. More particularly, in some examples, the spacing between adjacent grooves or ridges decreases to account for the increase in the angle of incidence (e.g., increase in the shallowness of the angle) of the light emanating from the light emitter 502. For purposes of explanation, the spacing of the lines in FIG. 8 has been exaggerated for emphasis in comparison with the spacing of the ridges or grooves shown in FIG. 5. As a result of the structure of the diffraction grating 504 of the illustrated examples, the uncollimated light emanating from the point source light emitter 502 may be redirected into directional light 120 at a controlled angle (e.g., substantially perpendicular to the window 102) defined by the structure of the diffraction grating 504 and relative placement of the light emitter 502. Without the diffraction grating 504, the light emitter 502 would illuminate the sample 104 while at a relatively small distance from the sample 104. However, the angle would not be consistent (e.g., directional) across the sample area. Furthermore, the shallow angle would increase the light propagation distance between the sample and sensor, and would make image reconstruction with symmetric resolution along the two sample dimensions difficult.

Figure 7:
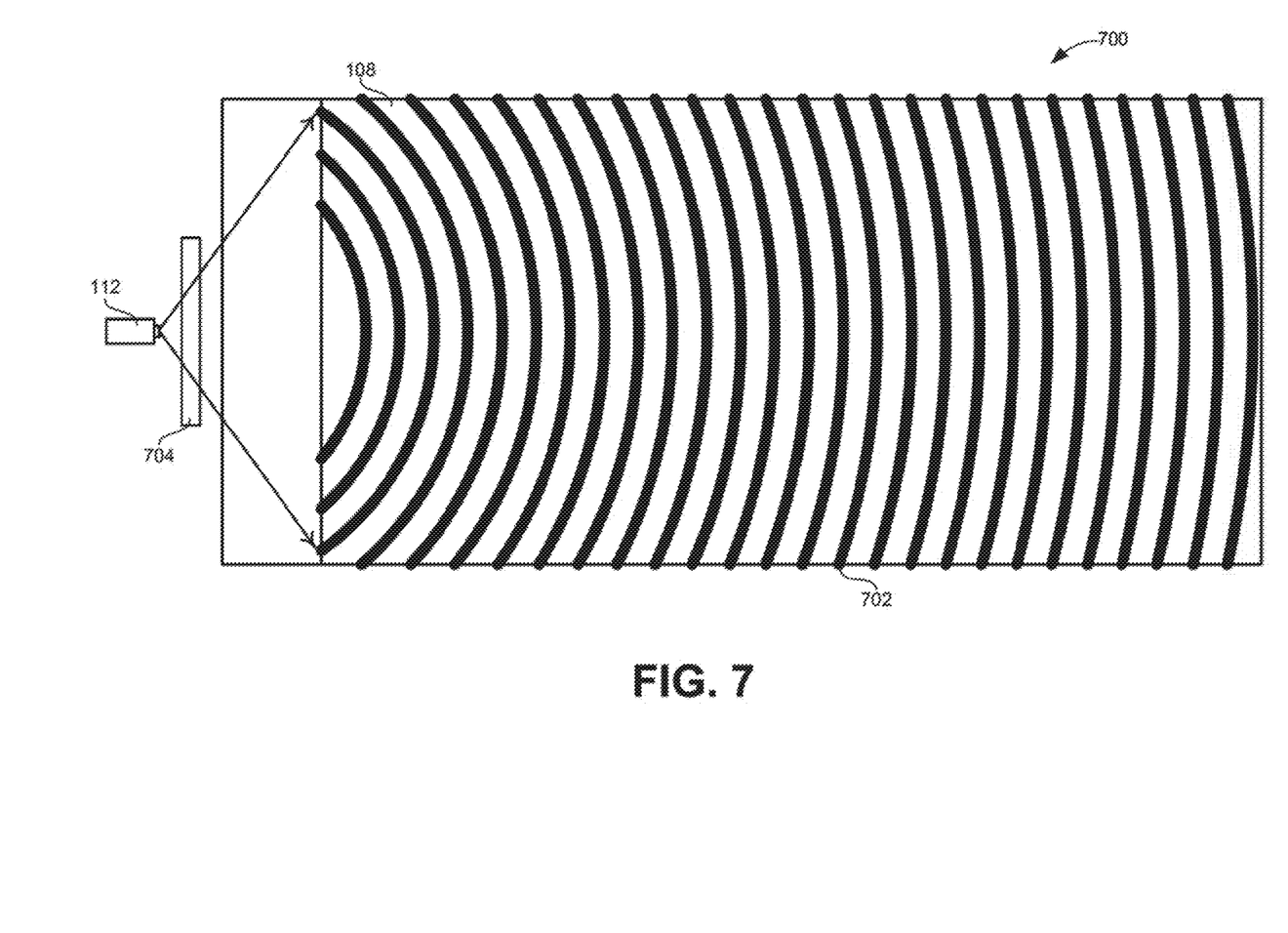
FIG. 7 is a top-view of another example microscopic imaging system constructed in accordance with the teachings disclosed herein.

FIG. 7 is a top-view of another example microscopic imaging system 700 constructed in accordance with the teachings disclosed herein. The example imaging system 700 of FIG. 7 is similar to the example imaging system 100 of FIGS. 1 and 2 in that light is propagated down a waveguide 108 to then interact with a diffraction grating 702. However, the example imaging system 700 of FIG. 7 is different than the imaging system 100 of FIGS. 1 and 2 in that the entire waveguide 108 may be provided with light from a single light emitter 112. As shown in the illustrated example, the light may be passed through cylindrical lens 704 to collimate the light in the vertical direction but not in the horizontal direction. That is, the light may be characterized by parallel rays travelling along the length of the waveguide 108 (similar to what is shown in FIG. 1) but the rays diverge from the light emitter 112 in the plane of the waveguide 108. Accordingly, as shown in the illustrated example, the grooves and/or ridges of the diffraction grating 702 are structured as circular arcs concentrically centered around the light source similar to the example system 500 of FIGS. 5 and 6. However, unlike FIGS. 5 and 6, the grooves of the diffraction grating 702 of the illustrated example of FIG. 7 are spaced with a constant period along the length of the waveguide 108 because of the vertically collimated nature of the light.

Figure 8:
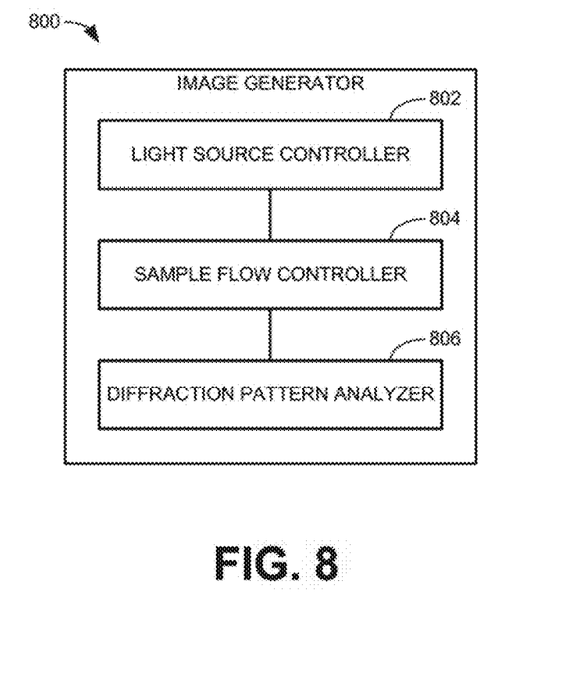
FIG. 8 is a block diagram of an example image generator constructed in accordance with the teachings disclosed herein to implement the example microscopic imaging systems of FIGS. 1-7.

FIG. 8 is a block diagram of an example image generator 800 constructed in accordance with the teachings disclosed herein to implement the example microscopic imaging systems 100, 300, 400, 500, 700 of FIGS. 1-7. In the illustrated example, the image generator 800 includes a light source controller 802, a sample flow controller 804, and a diffraction pattern analyzer 806.

In some examples, the light source controller 802 controls the light source used to illuminate the sample 104. In some examples, the light source controller 802 controls when the light emitter 112 is turned on. In some examples, the light source controller 802 controls the movement of the light emitter 112 relative to the collimating lens 116 (e.g., by operating the mechanical actuator 122). In some examples, where there are multiple light emitters 112 positioned at different angles relative to the collimating lens 116, the light source controller 802 controls the timing of each of the light emitters 112.

In the illustrated example of FIG. 8, the image generator 800 includes the sample flow controller 804 to control the flow of the sample 104 through a microfluidic system. For example, the sample flow controller 804 may control a microfluidic pump coupled to the microfluidic channel 404.

The image generator 800 of the illustrated example may be provided with the diffraction pattern analyzer 806 to analyze the image data captured by the image sensor 106. In particular, in some examples, the image data includes a diffraction pattern created by the interaction of the directional light 120 passing through the sample 104 and the light diffracted off of the sample 104. In some examples, the image data includes multiple diffraction patterns corresponding to the sample 104 being illuminated by the directional light 120 corresponding to different angles of incidence. In some examples, the diffraction pattern analyzer 806 implements algorithms to analyze the diffraction pattern(s) to generate or reconstruct an image of the sample 104.

While an example manner of implementing the image generator 800 is illustrated in FIG. 8, one or more of the elements, processes and/or devices illustrated in FIG. 8 may be combined, divided, re-arranged, omitted, eliminated and/or implemented in any other way. Further, the example light source controller 802, the example sample flow controller 804, the example diffraction pattern analyzer 806, and/or, more generally, the example image generator of FIG. 4 may be implemented by hardware, software, firmware and/or any combination of hardware, software and/or firmware. Thus, for example, any of the example light source controller 802, the example sample flow controller 804, the example diffraction pattern analyzer 806, and/or, more generally, the example image generator 800 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example light source controller 802, the example sample flow controller 804, and/or the example diffraction pattern analyzer 806 is/are hereby expressly defined to include a tangible computer readable storage device or storage disk such as a memory, a flash drive, a digital versatile disk (DVD), a compact disk (CD), a Blu-ray disk, etc. storing the software and/or firmware. Further still, the example image generator 800 may include one or more elements, processes and/or devices in addition to, or instead of, those illustrated in FIG. 8, and/or may include more than one of any or all of the illustrated elements, processes and devices.

Figure 9:
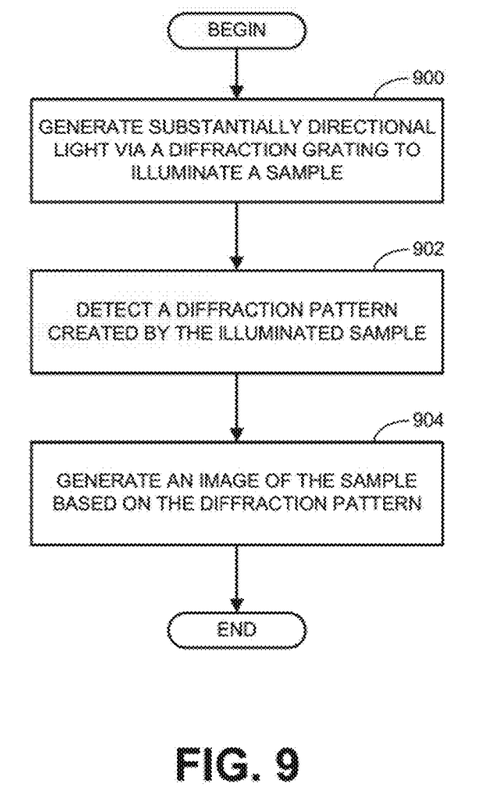
FIG. 9 is a flowchart representative of machine readable instructions that may be executed to implement the example image generator of FIG. 8, and/or, more generally, the example microscopic imaging systems of FIG. 1-7.

A flowchart representative of example machine readable instructions for implementing the image generator 800 of FIG. 8 and/or the example imaging systems 100, 300, 400, 500, 700 is shown in FIG. 9. In this example, the machine readable instructions include a program for execution by a processor such as the processor 1012 shown in the example processor platform 1000 discussed below in connection with FIG. 10. The program may be embodied in software stored on a tangible computer readable storage medium such as a CD-ROM, a floppy disk, a hard drive, a digital versatile disk (DVD), a Blu-ray disk, or a memory associated with the processor 1012, but the entire program and/or parts thereof could alternatively be executed by a device other than the processor 1012 and/or embodied in firmware or dedicated hardware. Further, although the example program is described with reference to the flowchart illustrated in FIG. 9, many other methods of implementing the example image generator 800 and/or the example imaging systems 100, 300, 400, 500, 700 may alternatively be used. For example, the order of execution of the blocks may be changed, and/or some of the blocks described may be changed, eliminated, or combined.

As mentioned above, the example process of FIG. 9 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process of FIG. 9 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

The program of FIG. 9 begins at block 900 where the example light source controller 802 generates substantially directional light via a diffraction grating (e.g., the diffraction grating 114, 302, 504) to illuminate a sample (e.g., the sample 104). At block 902, the example diffraction pattern analyzer 806 detects (e.g., via the image sensor 106) a diffraction pattern created by the illuminated sample. At block 904, the example diffraction pattern analyzer 806 generates an image of the sample based on the diffraction pattern. After the image is generated, the example program of FIG. 9 ends.

Figure 10:
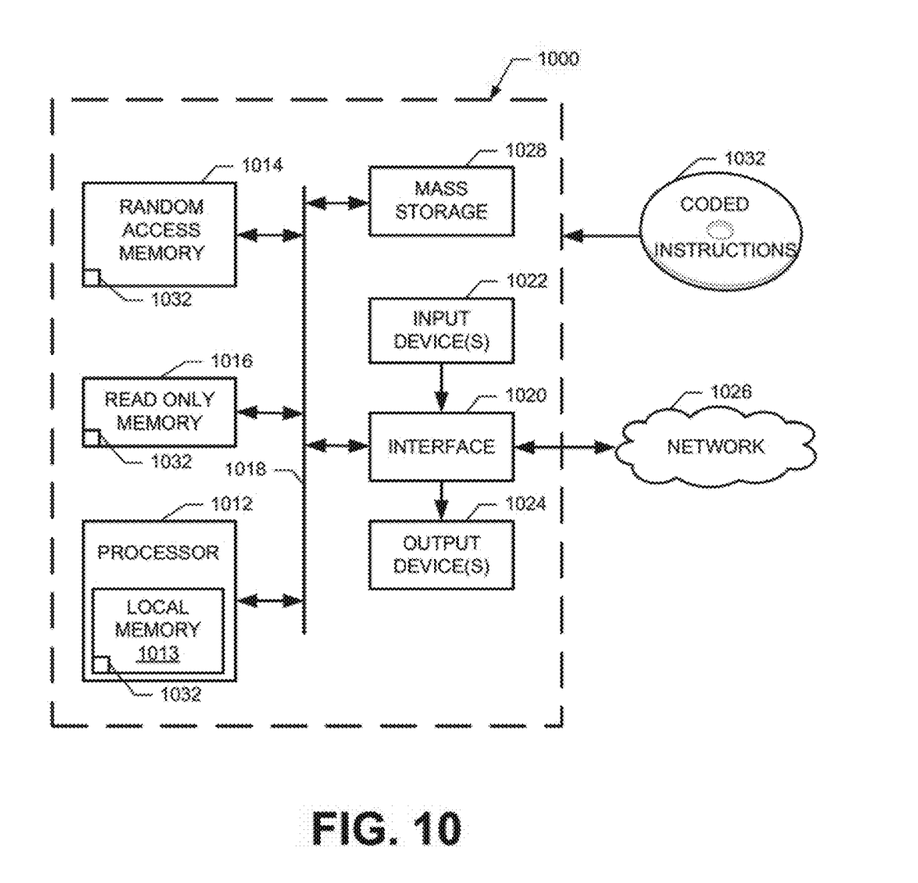
FIG. 10 is a block diagram of an example processor platform capable of executing the instructions of FIG. 9 to implement the example image generator of FIG. 8, and/or, more generally, the example microscopic imaging systems of FIG. 1-7.

FIG. 10 is a block diagram of an example processor platform capable of executing the instructions of FIG. 8 to implement the example image generator of FIG. 7, and/or, more generally, the example microscopic imaging systems of FIG. 1-6.

FIG. 10 is a block diagram of an example processor platform 1000 capable of executing the instructions of FIG. 8 to implement the example image generator of FIG. 7 and/or the example imaging systems 100, 300, 400, 500, 700 of FIGS. 1-7. The processor platform 1000 can be, for example, a server, a personal computer, a mobile device (e.g., a cell phone, a smart phone, a tablet such as an iPad™), a personal digital assistant (PDA), an Internet appliance, or any other type of computing device.

The processor platform 1000 of the illustrated example includes a processor 1012. The processor 1012 of the illustrated example is hardware. For example, the processor 1012 can be implemented by one or more integrated circuits, logic circuits, microprocessors or controllers from any desired family or manufacturer.

The processor 1012 of the illustrated example includes a local memory 1013 (e.g., a cache). The processor 1012 of the illustrated example may be in communication with a main memory including a volatile memory 1014 and a non-volatile memory 1016 via a bus 1018. The volatile memory 1014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 may be implemented by flash memory and/or any other desired type of memory device. Access to the main memory 1014, 1016 may be controlled by a memory controller.

The processor platform 1000 of the illustrated example also includes an interface circuit 1020. The interface circuit 1020 may be implemented by any type of interface standard, such as an Ethernet interface, a universal serial bus (USB), and/or a PCI express interface.

In the illustrated example, one or more input devices 1022 are connected to the interface circuit 1020. The input device(s) 1022 permit(s) a user to enter data and commands into the processor 1012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1024 are also connected to the interface circuit 1020 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1020 of the illustrated example, thus, typically includes a graphics driver card, a graphics driver chip or a graphics driver processor.

The interface circuit 1020 of the illustrated example also includes a communication device such as a transmitter, a receiver, a transceiver, a modem and/or network interface card to facilitate exchange of data with external machines (e.g., computing devices of any kind) via a network 1026 (e.g., an Ethernet connection, a digital subscriber line (DSL), a telephone line, coaxial cable, a cellular telephone system, etc.).

The processor platform 1000 of the illustrated example also includes one or more mass storage devices 1028 for storing software and/or data. Examples of such mass storage devices 1028 include floppy disk drives, hard drive disks, compact disk drives, Blu-ray disk drives, RAID systems, and digital versatile disk (DVD) drives.

The coded instructions 1032 of FIG. 8 may be stored in the mass storage device 1028, in the volatile memory 1014, in the non-volatile memory 1016, and/or on a removable tangible computer readable storage medium such as a CD or DVD.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
   a diffraction grating to redirect light from a light source toward a sample supported on a planar surface to thereby illuminate an area of the sample, the diffraction grating to be substantially parallel to the planar surface and aligned with the area of the sample when the light is redirected; and
   an image sensor to detect a diffraction pattern created by the illuminated sample the image sensor to be substantially parallel to the planar surface and aligned with the area of the sample when the light is redirected by the diffraction grating.

2. The apparatus of claim 1, further including a processor to analyze the diffraction pattern to generate an image of the sample.

3. The apparatus of claim 1, wherein the light is to provide directional illumination of the sample.

4. The apparatus of claim 1, further including a slab waveguide to carry the light from the light source to the diffraction grating.

5. The apparatus of claim 4, wherein the diffraction grating is adjacent a surface of the slab waveguide to face away from the sample.

6. The apparatus of claim 4, wherein the diffraction grating is adjacent a surface of the slab waveguide to face toward the sample.

7. The apparatus of claim 4, further including a collimating lens to collimate the light from the light source, the collimating lens to direct the light into the slab waveguide at an angle.

8. The apparatus of claim 7, wherein a position of the light source is adjustable relative to the collimating lens to vary the angle.

9. The apparatus of claim 1, further including:
   a microfluidic channel to contain the sample; and
   a pump to force the sample through the microfluidic channel.

10. The apparatus of claim 1, further including a housing containing the diffraction grating and the image sensor, the housing having a total height of one centimeter or less.

11. The apparatus of claim 1, wherein the image sensor includes a sensor array, the area of the sample corresponding to a size of the sensor array.

12. The apparatus of claim 1, further including a slab waveguide extending substantially parallel to and supporting the diffraction grating.

13. An apparatus comprising:
   a diffraction grating to diffract light toward a sample, the light from a light source, the light diffracted by the diffraction grating to be directional light such that different rays of the light diffracted by the diffraction grating are substantially parallel to one another;
   a slab waveguide to transmit the light from the light source to the diffraction grating, the diffraction grating positioned along a surface of the slab waveguide, the slab waveguide positioned adjacent the sample with the surface of the slab waveguide substantially parallel to a surface supporting the sample; and
   an image sensor to detect a diffraction pattern created from interference between a first portion of the directional light transmitted through the sample and a second portion of the directional light scattered by the sample.

14. The apparatus of claim 13, wherein the diffraction grating includes circular arced grooves.

15. The apparatus of claim 14, wherein the grooves are concentric about a central axis, the light source to be positioned on the central axis.

16. The apparatus of claim 15, wherein spacing between adjacent ones of the grooves is defined by a distance of the adjacent ones of the grooves from the light source.

17. The apparatus of claim 13, wherein the image sensor includes a sensor array, the sensor array being substantially parallel to the diffraction grating.

18. A method comprising:
   transmitting light through a slab waveguide toward a diffraction grating, the diffraction grating positioned along a surface of the slab waveguide;
   generating directional light via the diffraction grating to illuminate a sample, the directional light generated from the light transmitted through the waveguide, the light transmitted through the waveguide originating from a light source adjacent the diffraction grating;
   detecting, via an image sensor, a diffraction pattern created by the sample when illuminated by the directional light, the light to travel from the diffraction grating to the image sensor without passing through a lens, the image sensor being substantially parallel to the waveguide; and
   generating an image of the sample based on the diffraction pattern.

* * * * *